United States Patent [19]

Haber et al.

[11] Patent Number: 5,353,691
[45] Date of Patent: Oct. 11, 1994

[54] SELF-LUBRICATING PISTON FOR PHARMACEUTICAL CONTAINER

[75] Inventors: Terry M. Haber, Lake Forest; William H. Smedley, Lake Elsinore; Clark B. Foster, Laguna Niguel, all of Calif.

[73] Assignee: Habley Medical Technology Corp., Laguna Hills, Calif.

[21] Appl. No.: 47,976

[22] Filed: Apr. 14, 1993

[51] Int. Cl.⁵ ............................................. F01B 31/10
[52] U.S. Cl. ........................................ 92/159; 92/160; 92/247; 92/248; 92/249
[58] Field of Search ................ 92/155, 158, 159, 160, 92/240, 247, 248, 249, 250, 251

[56] References Cited

U.S. PATENT DOCUMENTS

| | | | |
|---|---|---|---|
| 331,831 | 12/1885 | Simpson et al. | 92/159 |
| 1,613,355 | 1/1927 | Miller | 92/250 |
| 1,882,156 | 10/1932 | Miller | 92/250 |
| 1,949,612 | 3/1934 | Mattair et al. | 92/159 |
| 2,211,456 | 8/1940 | Caldwell | 92/159 |
| 5,052,278 | 10/1991 | Smillie, III et al. | 92/155 |

*Primary Examiner*—Thomas E. Denion
*Attorney, Agent, or Firm*—Townsend & Townsend Khourie & Crew

[57] ABSTRACT

A compressible seal member is provided with peripherally distributed and axially spaced lubricant retaining grooves, or with radially extending lubricant channels in communication with a central lubricant reservoir. The sealing member has land portions and groove portions on the outer periphery, with the lubricant grooves or channels located along the groove portions. The seal member is installed within a pharmaceutical container with the tool having a working end received within a central aperture formed in the seal member so that the insertion forced is applied near the bottom end of the seal member to prevent compression during installation. When the pharmaceutical is expelled from the container, a plunger pushes on the accessible end of the seal member to compress the seal member axially and force the lubricant out of the grooves or channels and into contact with the inner wall surfaces of the container. The seal member provides a good friction fit during storage of the container to prevent leakage of the pharmaceutical and provides low sliding friction to permit smooth translatory motion of the seal member during expulsion of the pharmaceutical.

11 Claims, 2 Drawing Sheets

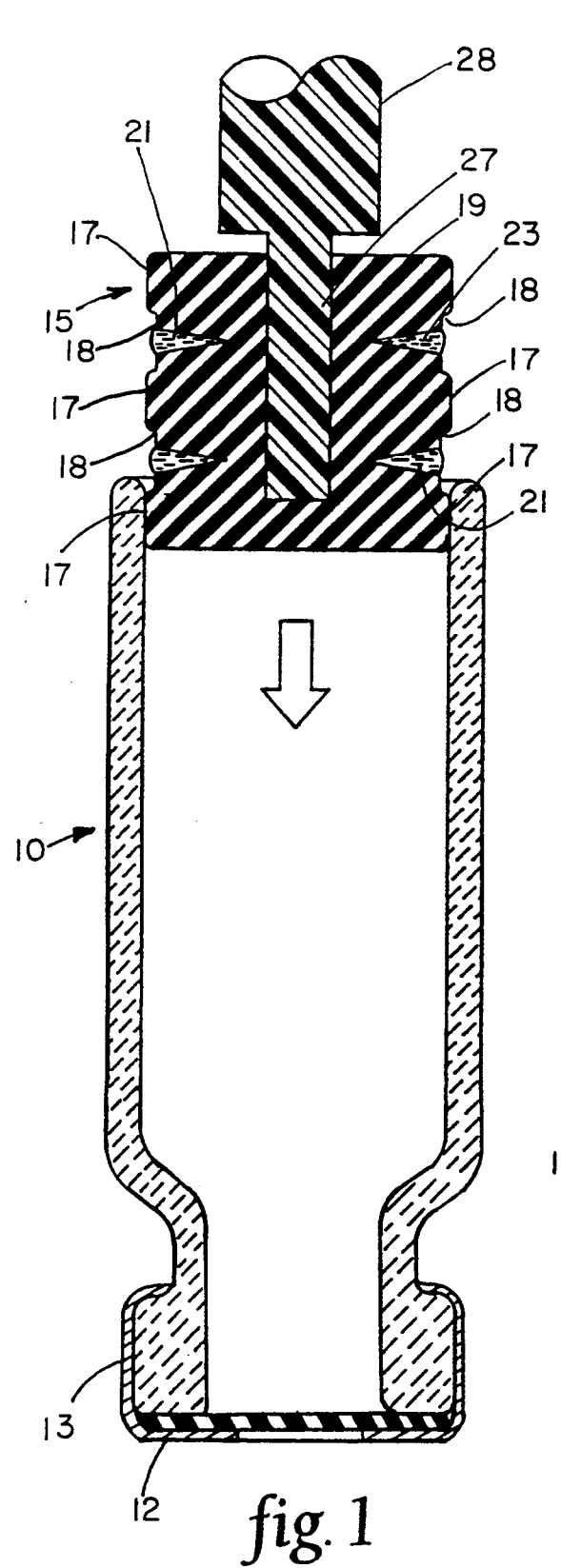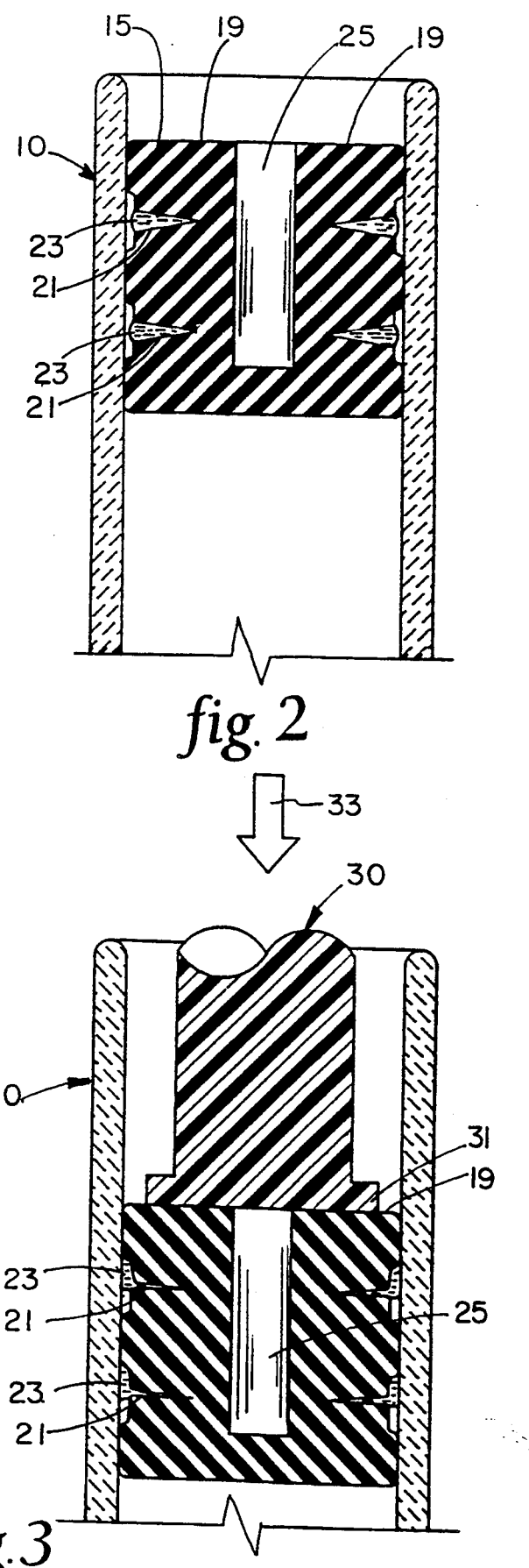
fig. 1
fig. 2
fig. 3

5,353,691

SELF-LUBRICATING PISTON FOR PHARMACEUTICAL CONTAINER

BACKGROUND OF THE INVENTION

This invention relates to pharmaceutical containers of the type having a seal for retaining a pharmaceutical within the container during storage and shipment and for expelling the pharmaceutical when ready for use.

Containers are known for packaging pharmaceuticals for storage, shipment and later use. In many such containers, one end of a typically cylindrical glass or pharmaceutically compatible plastic housing is sealed with a septum and closure band, while the other end is initially open to permit the container to be filled with the appropriate pharmaceutical. After filling, a piston-like seal is installed in the open end of the container in order to seal to the inner volume thereof. When the pharmaceutical is to be administered, the septum is typically penetrated with a needle and the pharmaceutical is expelled from the inside of the container by translating the seal along the axis of the container in the direction of the septum end using an appropriate tool, such as a push rod.

One of the problems encountered with pharmaceutical containers of the above type lies in the contrasting requirements for the seal: during storage and shipment, the seal must provide a tight seal to prevent leakage of the pharmaceutical outside of the confined volume of the container, while during expulsion of the pharmaceutical the seal should permit smooth translation along the inner wall surfaces of the container so that the pharmaceutical is evenly expelled without abrupt changes in the flow rate through the needle. Attempts to alleviate this problem and provide smooth translatory motion of the seal include coating the inside wall surfaces of the container with a lubricant. This solution suffers from the disadvantage that the lubricant contacts the pharmaceutical and may cause contamination, depending on the nature of the lubricant and the type of pharmaceutical stored in the container.

SUMMARY OF THE INVENTION

The invention comprises a self-lubricating seal member which provides a relatively high friction seal with the inner container wall surfaces but which also provides a relatively low sliding friction with the container walls when translated within the container.

The seal member includes a body portion with an outer periphery dimensioned to be accommodated within the interior of an associated pharmaceutical container and providing a secure fluid seal with the inner wall surfaces of the container. The body portion includes means for retaining a lubricant in such a manner that the lubricant does not contact the pharmaceutical within the container. In a first embodiment, the body portion is fabricated from a compressible material. Due to the compressible nature of the body portion, the lubricant is urged outwardly against portions of the inner surface of the container walls when the body portion of the seal member is compressed, which lubricates the seal member and provides a lower sliding friction between the seal member and the inner wall surfaces of the container, thereby promoting smooth translating motion.

In the first embodiment, the lubricant retaining means comprises a plurality of lubricant pockets formed in the outer periphery of the body portion of the seal member, the pockets being distributed about the outer periphery and axially spaced along the body portion. In a second embodiment, the retaining means comprises a lubricant reservoir formed within the body portion and accessible from outside the container when the seal member is installed, and a plurality of outwardly directed lubricant channels extending between the lubricant reservoir and the outer periphery of the seal member. In this embodiment, the body portion need not be compressible: the lubricant is expelled from the reservoir by means of a plunger having a piston-like tip which fits into the reservoir.

When cylindrical geometry is employed, the lubricant pockets comprise inwardly tapered grooves formed about the cylindrical outer periphery of the body portion of the seal member; while the lubricant channels extend radially between the reservoir and the cylindrical outer periphery of the body portion of the seal member. The outer periphery of the body portion of the seal member is preferably provided with land portions and groove portions, and the lubricant pockets and lubricant channels are formed in the groove portions.

The seal member further includes a central opening for receiving an insertion tool to enable the seal member to be installed within the container without undergoing substantial compression. The central opening may be either smooth walled or include a threaded portion engageable with a plunger.

In the first embodiment, the lubricant is first applied to the lubricant pockets, after which the seal member is installed within the container. In the second embodiment, the seal member may be first installed within the container and the lubricant added to the lubricant reservoir using a suitable delivery instrument, such as a pipette. The seal member provides a good friction fit and thus an effective fluid seal within the container when installed. When the first embodiment is translated axially of the container by applying pressure to the exposed surface, the seal member compresses, expelling the lubricant from the pockets so that the lubricant encounters the inner wall surface of the container and promotes smooth sliding translational motion as the seal is translated along the container. In the second embodiment, the lubricant is expelled from the reservoir by inserting the plunger tip into the reservoir.

For a fuller understanding of the nature and advantages of the invention, reference should be had to the ensuing detailed description taken in conjunction with the accompanying drawings.

BRIEF DESCRIPTION OF THE DRAWINGS

FIG. 1 is a sectional view illustrating a first embodiment of the invention;

FIG. 2 is a partial sectional view showing the seal member installed within the container prior to compression;

FIG. 3 is a partial sectional view illustrating the seal member after compression;

DESCRIPTION OF THE PREFERRED EMBODIMENTS

Figures 4, 5:
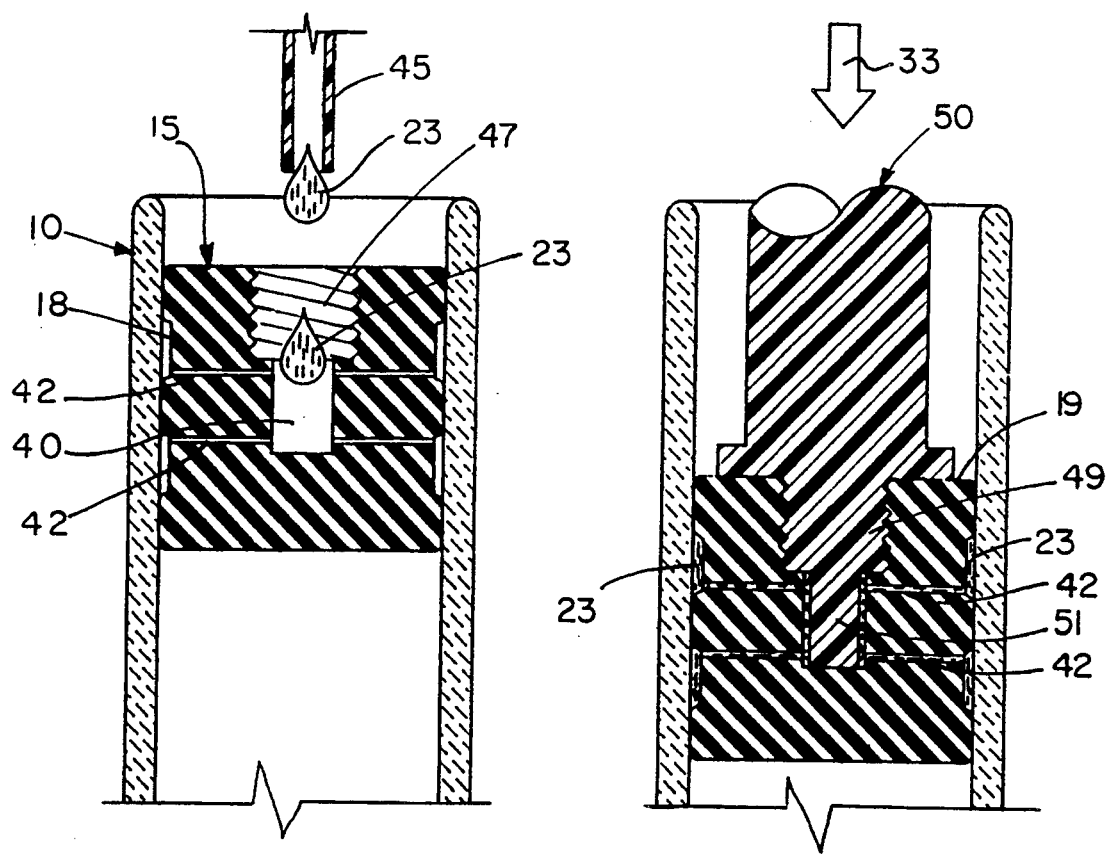
FIG. 4 is a partial sectional view illustrating an alternate embodiment of the invention after installation of the seal member.
FIG. 5 is a partial sectional view illustrating the FIG. 4 embodiment of the seal member after compression.

Turning now to the drawings, FIGS. 1-3 illustrate a first embodiment of the invention. As seen in FIG. 1, a pharmaceutical container 10 has a first end closed by a septum 12 and a closure band 13. Container 10 may be fabricated from glass or any suitable plastic which is relatively inert and non-reactive with pharmaceuticals intended to be contained therein. As viewed in FIG. 1, the upper end of container 10 is open to permit the container to be filled with a desired pharmaceutical. A seal member generally designated with reference numeral 15 is used to seal container 10 after the pharmaceutical has been added. Seal member 15 has geometry which is conformable with that of container 10—in the embodiment illustrated, substantially cylindrical geometry. Seal member 15 is fabricated from a compressible material, such as butyl rubber, latex or natural rubber and is provided with land portions 17 and groove portions 18 axially spaced along the outer periphery thereof. Formed within the groove portions 18 are inwardly tapering recesses 21 which provide lubrication pockets for storing a lubricant 23. Lubricant 23 is preferably a light viscosity lubricant, such as number 360 silicone lubricant available from Dow Corning and having a viscosity of 1 cs.

Lubricant 23 is preferably installed in lubricant pockets 21 prior to insertion of the seal member 15 by mounting the seal member 15 on a rotatable fixture, and rotating the seal member 15 while applying lubricant 23 to the recesses 21.

After the recesses 21 have been provided with the lubricant 23, the seal member 15 is installed within the interior of container 10 to the position illustrated in FIG. 2. In order to prevent any substantial compression of seal member 15 during installation within container 10, seal member 15 has a central aperture 25 dimensioned to accommodate the working end 27 of an installation tool 28. The axial length of aperture 25 is sufficient to enable the axial force from the use of tool 28 to be applied near the bottom end of seal member 15 so that only seal member 15 experiences only minimal compression during installation. The purpose for this arrangement is to maintain the lubricant 23 within the grooves 21 until such time as the seal member 15 is to be used to expel the pharmaceutical.

FIG. 3 illustrates the manner in which the lubricant 23 is forced against the inner wall surfaces of container 10 when the pharmaceutical is to be expelled through the septum 12. As seen in FIG. 3, a push rod 30 having a working end 31 of relatively large diameter (when compared to the diameter of the working end 27 of installation tool 28) is applied against the upper surface 19 of seal member 15. When axial force is applied in the direction of arrow 33, seal member 15 initially compresses in the axial direction, thereby forcing lubricant 23 out of the grooves 21 and against the inner wall surfaces of container 10. With additional force applied in the direction of arrow 33, seal member 15 begins to translate downwardly toward the septum end of container 10. With increased translatory movement, the land portions 17 of seal member 15 encounter the lubricated portions of the inner wall surface of container 10, thereby lowering the sliding friction and promoting smooth translatory motion of the seal member 15 along the axis of container 10.

FIGS. 4 and 5 illustrate an alternate embodiment of the invention in which the seal member 15 is provided with a centrally located lubricant reservoir 40 accessible from the top of container 10, and a plurality of radially extending lubricant channels 42 which communicate with the annular spaces formed between the groove portions 18 of seal member 15 and the confronting inner wall surface of container 10. In the embodiments of FIGS. 4 and 5, seal member 15 is first installed within the interior of container 10, after which the lubricant is applied by means of a suitable application, such as a pipette 45 held above the reservoir 40.

The embodiment of FIGS. 4 and 5 is provided with a threaded centrally located aperture 47 which is engageable by a threaded intermediate portion 49 of an expulsion plunger 50 to provide positive mechanical engagement therebetween. Plunger 50 has a tip portion 51 which fits within reservoir 40. In use, tip portion 51 is inserted into aperture 47 and portion 49 is threaded into aperture 47. As tip portion 51 advances into reservoir 40, the lubricant 23 is expelled from reservoir 40 thru channels 42 and into contact with the inner wall surfaces of container 10. It is noted that axial compression of the seal member is not required to lubricate the container wall surface in the embodiment of FIGS. 4 and 5.

While the above provides a full and complete disclosure of the preferred embodiments of the invention, various modifications, alternate constructions and equivalents may be employed as desired. For example, while cylindrical geometry has been illustrated, other geometries may be appropriate for specific container applications. In addition, the fabrication materials identified above are only exemplary, and other suitable materials may be substituted, as desired. Therefore, the above description and illustrations should not be construed as limiting the invention, which is defined by the appended claims.

What is claimed is:

1. A piston for a pharmaceutical container comprising:
   a container having an open end, a closed end, and a wall structure having an inner surface, the container having a longitudinal axis;
   a seal member having an upper side, comprising a compressible material, and being at least partially positioned within the container between the open end and closed end, the seal member also having an outer periphery and means for retaining a lubricant, the outer periphery being dimensioned to provide sealing engagement with said inner surface of said wall structure;
   a lubricant contained within said means for retaining a lubricant; and
   means for exerting a longitudinally-directed force on the seal member and at least partially compressing the seal member in the direction of the longitudinal axis, said exerting means compressing said retaining means and forcing said lubricant from said retaining means and into contact with said inner surface of said container when said seal member is at least partially compressed in the direction of the longitudinal axis.

2. The invention of claim 1 wherein said retaining means comprises a plurality of lubricant pockets formed in said outer periphery.

3. The invention of claim 2 wherein said pockets are distributed about the outer periphery and axially spaced along said seal member.

4. The invention of claim 2 wherein said seal member has substantially cylindrical geometry forming a substantially cylindrical periphery, and wherein said lubricant pockets comprise inwardly tapered grooves formed about the cylindrical outer periphery.

5. The invention of claim 2 wherein said outer periphery is provided with land portions and groove portions; and wherein said lubricant pockets are formed in the groove portions.

6. The invention of claim 1 wherein said seal member further includes a central opening for receiving an insertion tool.

7. A piston for a pharmaceutical container comprising:
   a container having an open end, a closed end, and a wall structure having an inner surface;
   a seal member positioned within the container, comprising;
      means for retaining a lubricant,
      an outer periphery dimensioned to provide sealing engagement with said inner surface of said wall structure,
      a lubricant reservoir in fluid communication with ambient,
      a plurality of lubricant channels fluidly coupled to the lubricant reservoir, the lubricant channels extending between said lubricant reservoir and said outer periphery; and
   a plunger configured to drivingly engage the seal member, the plunger including means for displacing a lubricant introduced into the lubricant reservoir so that said lubricant is forced through said plurality of lubricant channels and into contact with said inner surface of said container.

8. The invention of claim 7 wherein said lubricant channels are distributed about the outer periphery and axially spaced along said body portion.

9. The invention of claim 7 wherein said body portion has substantially cylindrical geometry forming a substantially cylindrical outer periphery, and wherein said lubricant channels extend radially between said reservoir and said cylindrical outer periphery.

10. The invention of claim 7 wherein said outer periphery is provided with land portions and groove portions; and wherein said lubricant channels are formed in the groove portions.

11. The invention of claim 7 wherein said seal member comprises a threaded portion configured to engage said plunger.

* * * * *